(12) United States Patent
Wakikaido et al.

(10) Patent No.: US 6,451,014 B1
(45) Date of Patent: Sep. 17, 2002

(54) ELECTRODE DEVICE FOR MICROWAVE OPERATION

(75) Inventors: Koichi Wakikaido, Yao; Suminori Kitada, Kasukabe, both of (JP)

(73) Assignee: Azwell, Inc., Osaka (JP)

( * ) Notice: Subject to any disclaimer, the term of this patent is extended or adjusted under 35 U.S.C. 154(b) by 0 days.

(21) Appl. No.: 09/508,247

(22) PCT Filed: Jun. 5, 1999

(86) PCT No.: PCT/JP99/03641

§ 371 (c)(1),
(2), (4) Date: Mar. 9, 2000

(87) PCT Pub. No.: WO00/02492

PCT Pub. Date: Jan. 20, 2000

(30) Foreign Application Priority Data

Jul. 9, 1998 (JP) .......................................... 10-210444

(51) Int. Cl.[7] .............................................. A61B 18/04
(52) U.S. Cl. .............................. 606/33; 606/34; 606/37; 606/39; 606/40; 606/41; 607/101
(58) Field of Search ............................ 606/34, 37, 39, 606/40, 41–50, 110, 113, 162; 600/141, 142, 149

(56) References Cited

U.S. PATENT DOCUMENTS

| 5,314,466 A | | 5/1994 | Stern .......................... 607/156 |
| 5,441,499 A | * | 8/1995 | Fritzsch ....................... 606/45 |
| 5,848,986 A | * | 12/1998 | Lundquist et al. ..... 604/164.11 |

FOREIGN PATENT DOCUMENTS

| JP | 1-175827 | 7/1989 |
| JP | 5-501065 | 3/1993 |
| JP | 7-184904 | 7/1995 |
| JP | 8-164141 | 6/1996 |
| JP | 10-14860 | 1/1998 |

* cited by examiner

Primary Examiner—Rosiland S. Kearney
(74) Attorney, Agent, or Firm—Millen, White, Zelano & Branigan, P.C.

(57) ABSTRACT

An electrode device is for microwave coagulation therapy disclosed in which the direction of its electrode tip can be controlled by operation in its proximal region. The device comprises: a handpiece provided with a rigid hollow support shaft extending toward a distal end, a movable support provided at the distal end of the support shaft and carrying thereon an electrode, a coaxial cable which is connected at its proximal end to a coaxial connector and extending through the support shaft and connected in the movable support to the electrode, wherein: (a) the movable support comprises one or more links each surrounding the coaxial cable and longitudinally connected to the distal end of the support shaft so that the movable support can be bent and stretched in a single plane, and (b) the electrode device comprises a resilient stiff member fixed at one of its end to the deflection side of the most distal one of the links composing the movable support and extending through the support shaft and so connected at its proximal end to a control section of the handpiece that the resilient stiff member can be pulled and pushed back at the proximal end of the handpiece.

7 Claims, 8 Drawing Sheets

ELECTRODE DEVICE FOR MICROWAVE OPERATION

TECHNICAL FIELD

The present invention relates to an electrode device used in microwave surgery apparatus, with which coagulation, hemostasis, ablation, etc. of biotissues is performed by means of microwave, and more specifically to an electrode device in which the direction of the electrode fixed at the distal end of an elongated shaft can be controlled at a proximal site of the shaft.

BACKGROUND ART

For treatment of pathological tissues, e.g., malignant tumors, which are located deep in a body, methods which have been widely applied are those by which the body is deeply cut open through the skin to expose the lesion and then the lesion is excised together with the adjacent tissues. In recent years, however, due to a trend for benefit of patients quality of life, treatment methods that do not involve abdominal section and could thereby shorten the term of hospitalization are becoming familiar. Among them, examples of methods for treatment of hepatocellular carcinoma include transcatheter arterial embolization (TAE), percutaneous ethanol injection (PEI), microwave coagulation therapy (MCT).

In microwave coagulation therapy, selective coagulation, hemostasis, ablation, etc. of the lesion are performed utilizing the dielectric heat generated in the bio-tissues due to a localized microwave electromagnetic field created between electrodes applied to the lesion site by radiating microwave at a predetermined frequency between the electrodes. It has advantages over coagulation or ablation procedures using an electric or laser knife in hemostatic and coagulation effects, as well as in its easiness of handling. For microwave coagulation for deep region of the body, there are known methods such as percutaneous microwave coagulation therapy (PMCT) and laparoscopic microwave coagulation therapy (LMCT). In laparoscopic microwave coagulation therapy, surgery is performed by creating in the abdominal surface multiple openings usually with a diameter of several mm at proper locations surrounding the umbilicus, then inserting, through respective trocars, through one of which a laparoscope with a CCD camera equipped at its distal end, through two of which forceps, and through another of which a surgical electrode, and introducing a nontoxic gas such as carbon dioxide into the abdominal cavity to inflate the abdomen, and then manipulating the surgical electrode from outside of the body while watching the image captured by the CCD camera and displayed on a monitor.

When the electrode is being inserted through the trocar into the abdominal cavity, the electrode and the supporting shaft used for laparoscopic microwave coagulation therapy must be in generally straight configuration. Thus, the conventional electrode has an integrally attached straight shaft and the direction of its electrode tip is fixed. On the other hand, the location of a lesion to be coagulated may vary even with regard to the same organ, and there are cases in which blood vessels or the bile duct not to be coagulated lie in front of the lesion. With a conventional electrode, which is attached to the supporting shaft in a fixed, generally straight configuration, therefore, it has often been difficult to apply the electrode at an optimal angle to the lesion.

To solve this problem, it is necessary to design an electrode such that, after insertion of it into the abdominal cavity, the direction of the electrode can be changed to a desired angle by operation at a proximal site. However, unlike an electric or laser knife, one of the characteristics of an electrode for microwave coagulation therapy is that it contains inside a microwave coaxial cable up to the distal end of the electrode. Due to this, there has been proposed no electrode usable in laparoscopic microwave coagulation therapy in which the direction of its electrode tip can be controlled at its proximal site.

That is, there is a difficulty with an electrode for microwave coagulation therapy in providing within its support shaft a complex mechanism for controlling the angle of the electrode, for a coaxial cable occupies main space in the cross section of the support shaft's lumen.

In addition, it is one of the characteristics of a microwave coaxial cable that if there is a region curved at an acute angle, the microwave being conducted is partly reflected at the region to create a standing wave, thus causing generation of heat and a loss of energy, and the forward conduction of microwave energy beyond that region is eventually impeded. Therefore, even when the electrode is bent near its distal end, its curve must not be acute so that the curve of the interior coaxial cable can have as large a radius of curvature as possible.

Furthermore, a microwave coaxial cable extending contained within the shaft includes a inner conductor, an insulating medium covering the inner conductor, and an outer conductor surrounding the insulating medium. Thus, as a coaxial cable has substantial thickness and therefore resists deformation, a mechanism that can apply a sufficient force on it is required for bending it.

Furthermore, as the electrode is inserted into or pressed against a lesional tissue, the electrode must be so constructed that the angle of the electrode can be retained even when the electrode receives a reaction force from the tissue.

Still further, as tissue coagulation with microwave generally takes about 60 seconds per site, the electrode once applied to the lesion site must be held at the predetermined angle during the period. Therefore, it is preferable that the electrode is so designed that the angle is fixed without imposing extra burden on the hand of the operator once the direction of electrode is set at an desired angle.

In addition, further problem was noticed that while the support shaft containing a coaxial cable is being bent, the interior coaxial cable caused to curve is often distorted along the longitudinal axis, thus creating stress in the direction of the longitudinal axis, and this stress could prevent smooth bending of the shaft beyond a certain amount of bending.

The objective of the present invention is to solve the above mentioned problems and provide an electrode for microwave coagulation therapy, in which the direction of the electrode tip can be controlled as desired through operation at its proximal region.

DISCLOSURE OF INVENTION

The present inventors found that, according to a planned maximal angle with the distal end of the electrode, by separating the distal part of support shaft of the electrode into one or more links whose angles can be altered in a single plane, and arranging them so that the most distal one of the links can be pulled and pushed back on its deflection side from a proximal region by means of an elongated resilient member along the inner surface of the support shaft, the direction of the distal end of the electrode containing a coaxial cable can be easily and reliably controlled from the proximal region of the electrode, and, even where multiple links are included, all of the links can be moved in concert retaining their mutual balance and therefore an acute curve will not created in any region along the coaxial cable contained therein even when the angle of the electrode is changed a great deal.

Thus, the present invention provides an electrode device for microwave surgery which allows to control the angle of the electrode thereof comprising: a handpiece provided with a rigid hollow support shaft extending toward a distal end, a movable support provided at the distal end of the support shaft and carrying thereon an electrode for microwave surgery, a microwave coaxial cable which is connected at the proximal end thereof to a microwave coaxial connector and connected in the movable support to corresponding portions of the electrode for microwave surgery, said cable extending through the handpiece and the support shaft, wherein:

(a) the movable support comprises one or more links surrounding the coaxial cable and longitudinally connected to the distal end of the support shaft so that the movable support can be bent and stretched, in a single plane, between the direction of the longitudinal axis of the support shaft and a direction deflected therefrom, and (b) the electrode device further comprises a resilient stiff member fixed at one end thereof to the deflection side of the most distal one of the links composing the movable support and so connected to a control section of the handpiece movable from outside that the resilient stiff member can be pulled and pushed back at the proximal end of the handpiece, said resilient stiff member extending through the support shaft.

In laparoscopic microwave coagulation therapy, the electrode device of the present invention in the above configuration can be kept stretched straight when being introduced into a trocar inserted into the abdominal cavity, and then, after a predetermined length of its distal part has been inserted out of the trocar into the abdominal cavity, can be manipulated as required, by operating the control section provided in the handpiece, to adjust the direction of the electrode tip to be adapted to the location of the lesion. In addition, although it depends on a mechanism by which both pulling and pushing force are applied only to the most distal one of the links, all of the links can be moved in concert while retaining their mutual balance, even where the movable support is composed of multiple links. Thus, concentration of curvature will not occur to a limited region of the movable support, and therefore creation of an acute curve will be avoided at any region along the coaxial cable contained therein even when the angle of the electrode is changed a great deal. With such configuration and functions, the present invention allows to control the direction of the electrode tip within the abdominal cavity as desired by proximal manipulation during microwave coagulation therapy, thereby enabling more flexible operation in accordance with the location of the lesion to be coagulated and with conditions of the surrounding tissues.

When changing the direction of the electrode tip greatly, depending upon the mutual positioning of the contained coaxial cable, the links and the support shaft, there may be cases in which the coaxial cable is strained or compressed along the longitudinal axis and thus created substantial longitudinal stress hinders a smooth manipulation of the electrode tip. To address this problem, the present inventors found that by arranging the coaxial connector positioned in the handpiece to be able to sift, e.g., slide, along the longitudinal axis within a predetermined range rather than fixing it to the handpiece, any conceivable stress along the longitudinal axis of the coaxial cable can be released and thus allowing a smooth manipulation of the electrode tip without being hindered even for a great deal of change in its angle of, e.g. up to 180°.

Therefore, the present invention further provides an electrode device for microwave surgery as described above and further characterized in that the coaxial connector is attached to the handpiece in such a manner that it can shift along the longitudinal axis within a predetermined range so that it can follow a longitudinal shift of the coaxial cable in association with the movement of the movable support between the deflected and the stretched positions.

With this additional feature, even when the angle of the electrode tip is changed a great deal by bending the movable support, no stress is created in the coaxial cable along its longitudinal axis because the coaxial connector, to which the proximal end of the coaxial cable is connected, may shift, e.g., by sliding, in the direction of the longitudinal axis relative to the handpiece in response to the longitudinal shift which may take place in the coaxial cable within the support shaft. Therefore, the angle of the electrode tip can be changed up to as much as 180° without causing any problem.

BEST MODE FOR CARRYING OUT THE INVENTION

Figure 1:
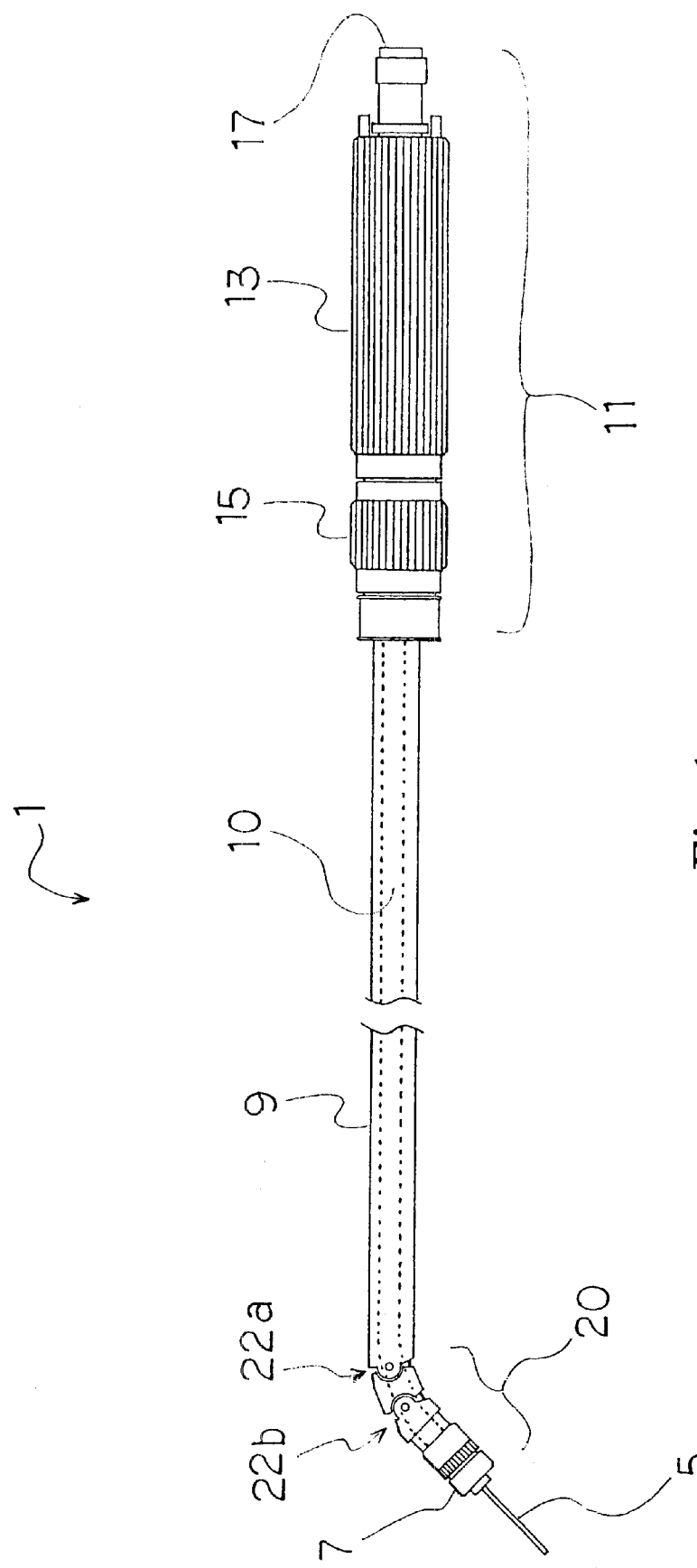
FIG. 1 illustrates a schematic side view of the electrode for microwave coagulation therapy.

In the present invention, even where the movable support carrying the electrode is composed of multiple links, it is enough to fix the resilient stiff member at its end onto the deflection side of the most distal one of the links only, without fixing it to intermediate links. The remaining links may simply be in longitudinally slidable contact with the resilient stiff member extending to the handpiece. The resilient stiff member may be fixed to the most distal one of the links on its deflection side, and, e.g., on the inner surface of that side. Though fixation may be performed by conventional means, it is preferred not to adopt bulky means, for a coaxial cable is to be inserted into the link. Fixation may be carried out, for example, by making a bore in the link and the resilient stiff member at the sites where they are mutually linked, laying them upon each other, inserting a pin through the bore and caulking the end of the pin.

In the present invention, the "resilient stiff member" may be made of a material that can transmit, to the deflecting side of the most distal one of the links, pulling and pushing-back force applied by the control section, and withstands repetitive bending and stretching. A resilient metal belt or metal wire (either simple or stranded wire), for example, may be used for this purpose. When a metal wire is employed as a resilient stiff member, for preventing flexure while being pushed back toward the distal end, a path may be provided along the inner surface of the support shaft as desired which serves as a guide. When a metal belt is employed as a resilient stiff member, a guide provided for a metal wire may not be necessary, for the flexure of the metal belt while being pushed back is restricted because the coaxial cable occupies substantial space in the lumen of the support shaft. Again, when a metal belt is employed, it may be allowed that a metal belt is employed only for the part extending through the movable support carrying the electrode, with more proximal part being thicker and made of metal plate or a metal stick.

The resilient stiff member, one of whose ends is fixed to the most distal one of the links composing the movable support, extends through the remaining links of the movable support and through the support shaft toward the handpiece and is connected at the proximal end to the control section, which is movable from outside, to allow pulling and pushing-back of the resilient stiff member. The configuration of the control section movable from outside and the manner of its connection to the proximal end of the resilient stiff member are not limited insofar as they are suitable to be operated with a hand holding the handpiece. For this part, it may be possible to employ some proper means known to those skilled in the art concerning a similar surgical device. However, a mechanism in which the movable support is bend by squeezing a lever provided on the handpiece would impose a burden on the operator who must keep the angle of the movable support for the time of effecting coagulation, usually about 60 sec per site.

In order for making it easy to keep the angle of the movable support for a certain length of time, a preferable system is that in which the control section is made of an internally threaded member which is fit around a tubular shaft section of the handpiece and prohibited from longitudinal shifting and which can be rotated from outside, wherein the thread of the internally threaded member associates with the proximal end of the resilient stiff member by a screw mechanism so that a rotation of the internally threaded member is converted to a shift in the longitudinal direction of the proximal end of the resilient stiff member. There are known a wide variety of screw mechanisms that convert a rotational motion to a linear motion, and therefore a suitable mechanism can be readily chosen by those skilled in the art. With such a screw mechanism, once the angle of the movable support is adjusted, the angle of the movable support is kept even if the control section is left unsupported with fingers, which provides a great benefit to the operator.

A more specific example of such a system is one in which an internally threaded member made of a tubular member internally threaded is adopted as the control section, which is rotatably fit around a tubular shaft section(which may be an extended part of the support shaft) of the handpiece but in such a manner that a shift in the longitudinal direction is prohibited, the tubular shaft section being provided with a longitudinal slot, the proximal end of the resilient stiff member being fixedly provided with a projection directed radially outwardly, and the projection protruding out of the slot and thereby engaging with the thread of the internally threaded member of the control section. The projection may be made on the proximal end of the resilient stiff member in any convenient manner. For example, it may comprise a pin fixed in a bore defined at the proximal end of the resilient stiff member. In this case it is enough that the pin is of such length and shape that one end of the pin protrudes out of the slot and engages with the thread of the internally threaded member. In order to prevent the pin from retracting into the interior of the tubular member and thereby disengaging from the thread, the lower part of the pin protruding out of the slot may be made thicker than the slot or the part may be provided with a secured washer.

In a system in which a projection at the proximal end of the resilient stiff member is engaged with the thread of the internally threaded member, by rotating the internally threaded member of the control section with fingers of the hand holding the handpiece, the projection engaging with the thread is moved back and forth, and this movement is transmitted to the most distal link which is connected to the distal end of the resilient stiff member, and, consequently, the amount of the curve of the movable support is changed. Because a screw mechanism is adopted, the movement of the resilient stiff member is small compared with the rotation of the control section, and therefore a fine control of the curve of the movable support is made with ease. On the contrary, for a given change in the curvature of the movable support, the required amount of a corresponding rotation of the internally threaded member of the control section is much greater, an external force imposed on the electrode tip cannot cause rotation of the internally threaded member of the control section. Therefore, once the movable support is bent to a required degree by operating the control section, the control section stays fixedly in the same position even if it is left unsupported with fingers. Therefore, it is not necessary for the operator to continue to apply a force on the control section to keep the curvature of the movable support, and thus no inconvenience is caused to the intended surgical operations such as coagulation.

The one or more links composing the movable support may be connected longitudinally to the distal end of the support shaft so that the movable support can be repeatedly bent and stretched, in a single plane, between the direction of the longitudinal axis of the support shaft and a direction deflected therefrom. One of the particularly preferable examples of the wide variety of such configurations comprises turning pairs which are mutually pivotal around an axis perpendicular to the axis of the support shaft and composed with adjacent movable links or together with the support shaft. Specifically, this may be embodied, for example, by defining flat planes on both sides which overlap between adjacent links or the adjacent support shaft, and connecting each of those overlapped projected plates with a pin.

EXAMPLE

The present invention is described in further detail below with reference to a typical example. However it is not to intended that the present invention be restricted to the example.

FIG. 1 illustrates a schematic side view of an example of the electrode device for microwave coagulation therapy. While the illustrated example is a so-called monopolar type electrode, a bipolar type electrode may also be used and the shape of the electrode tip may be in a variety of shapes such as ball-like, hook-like, sickle-like or blade-like shapes, since the type or shape of the electrode tip is irrelevant to the present invention. In the figure, 1 indicates an electrode device for microwave coagulation therapy, 5 is a central electrode, and 7 is a tubular ground electrode. 9 is a rigid hollow support shaft made of a metal with a circular cross section, through the interior of which extends a flexible coaxial cable 10 for microwave shown in phantom lines. 11 is a handpiece which is to be held in a hand of the operator when handling the electrode. The handpiece 11 includes a holding grip 13, an angle control ring 15, which is the control section for adjusting the angle of the electrode tip, a microwave coaxial connector 17 for introducing microwave of a predetermined frequency from a microwave generation apparatus such as a magnetron. At the distal end of the support shaft 9 is provided a movable support 20 containing in itself the flexible coaxial cable 10 extending therethrough. In the figure, the movable support 20 is shown in its curved position. While the movable support has two joints 22a and 22b and thereby consists of two links in the illustrated example, the number of joints (and therefore the number of the movable links) may be chosen in manufacture as desired in accordance with the intended maximal angle of the electrode tip (maximal curvature of the movable support). For example, when the intended maximal angle of the electrode is 45°, a single joint is enough. However, two joints would provide a comparatively smooth control, and also the curve of the contained coaxial cable would be less acute. And when it is aimed to provide an electrode that can be bent within a wide range, the purpose can be met simply by increasing the number of joints to two, three, four, five and so on. For example, though change in angle of up to about 90° is possible by providing two joints, three or more links may be provided to make the angle of each link less acute. It is possible to make a electrode tip deflectable about 180° by providing four or more links. In such a configuration, it becomes possible to coagulate a lesion located on the back side of the organ from the viewpoint of the operator as the central electrode can be deflected in the direction of the operator. While there is no definite upper limit with regard to the number of the joints (therefore to the number of the links), it is practical to limit the maximal number up to six, considering the cost of manufacturing.

Figure 2:
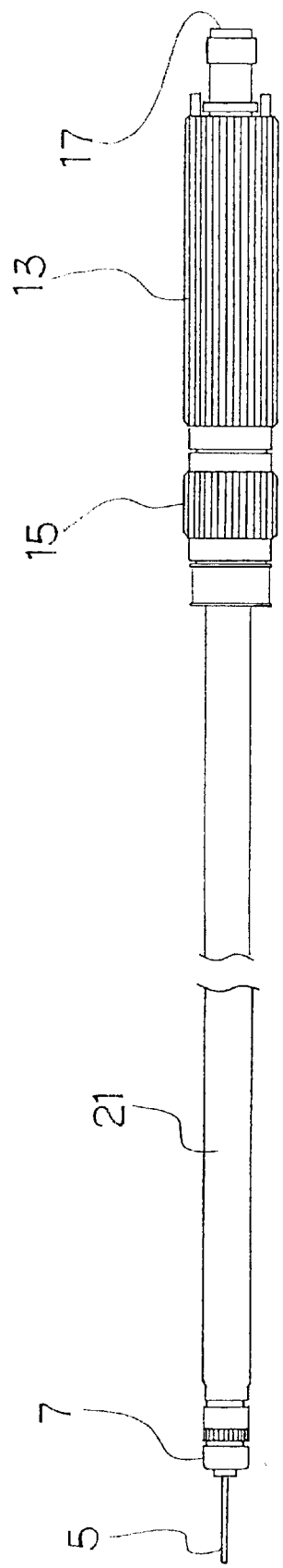
FIG. 2 illustrates a side view of the electrode device when supplied for use for microwave coagulation therapy.

When put into practical use, the support shaft 9 and the movable support 20 of the electrode device of the present invention are covered with an insulating, elastic and soft integral cover 21, which is similar to one adopted for conventional electrodes for microwave surgery, as shown in FIG. 2.

Figure 3:
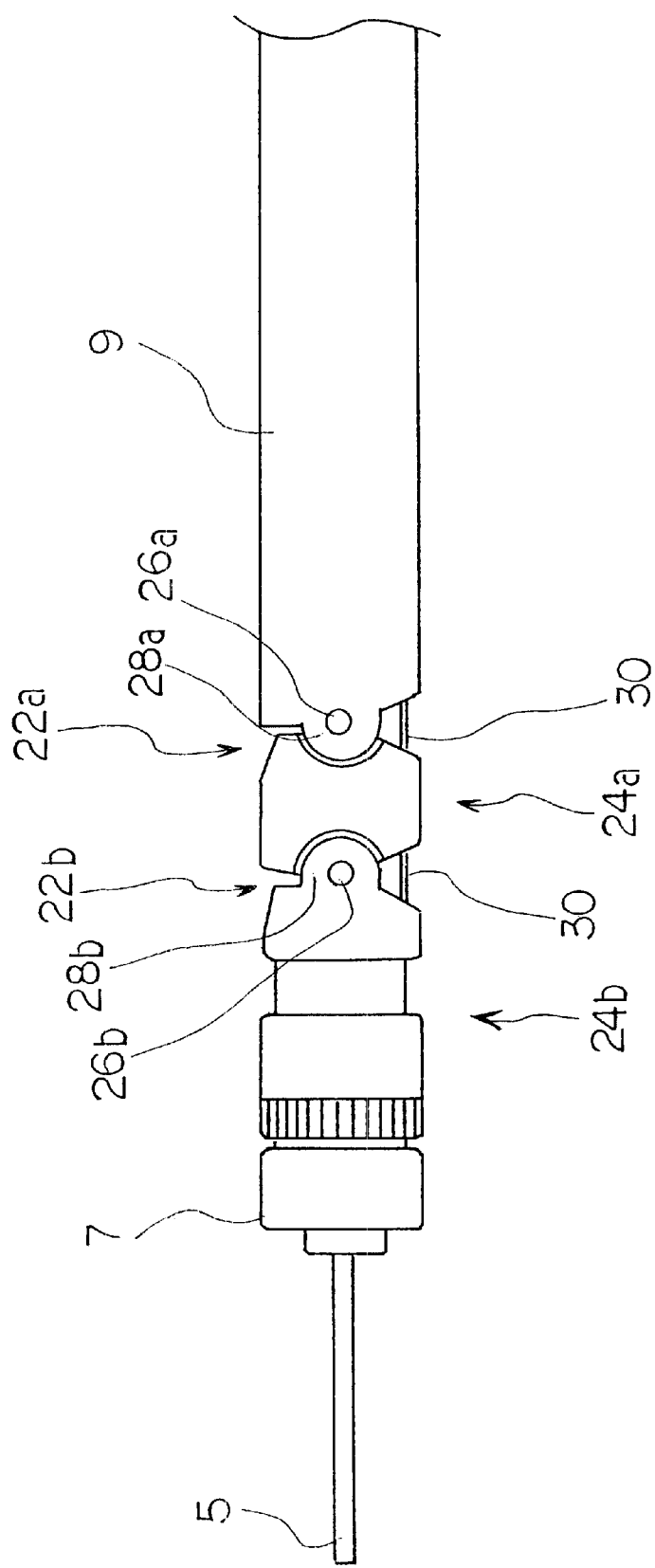
FIG. 3 illustrates an enlarged side view of and around the movable support.

FIG. 3 is an enlarged side view illustrating in more detail the structure of the movable support 20, with its cover 21 removed. In the figure, the movable support 20 is shown in its stretched position, and 24a and 24b, which are the links composing the movable support 20, have a generally circular cross-section. The most distal link 24b is fixedly provided with a central electrode 5 and a tubular ground electrode 7. The link 24a is connected to the support shaft 9 at the joint 22a, and the link 24b is connected to the link 24a at the joint 22b. At the joint 22a providing connection between the support shaft 9 and the link 24a, a pin 26a pivotally connects an extended portion 28a of the support shaft 9 to part of the link 24a (in the figure, the part lies on the back surface of the extended portion 28a of the support shaft 9). At the joint 22b providing connection between the links 24b and 24a, a pin 26b pivotally connects an extended portion 28b of the link 24b to part of the link 24a (in the figure, the part lies on the back surface of the extended portion 28b of the link 24b). The movable support is of a symmetrical shape relative to the plane of FIG. 3, and the same structure of the joints is provided at the back of the figure.

With further reference to FIG. 3, 30 is a spring member, which is fixed near its distal end with a pin to the inner surface of the bottom wall (i.e., deflection side) of the link 24b and extends along the inner bottom surfaces of the link 24a and the support shaft 9 to the handpiece 11. The spring member 30 is not secured to the link 24a. The part of the spring member contained within the movable support 20 is in the shape of a thin belt as illustrated, but its part contained within the support shaft is made thicker in the form of a plate. This shape given to the spring member 30 is beneficial in minimizing a flexure when pushed back in the distal direction.

Figure 4:
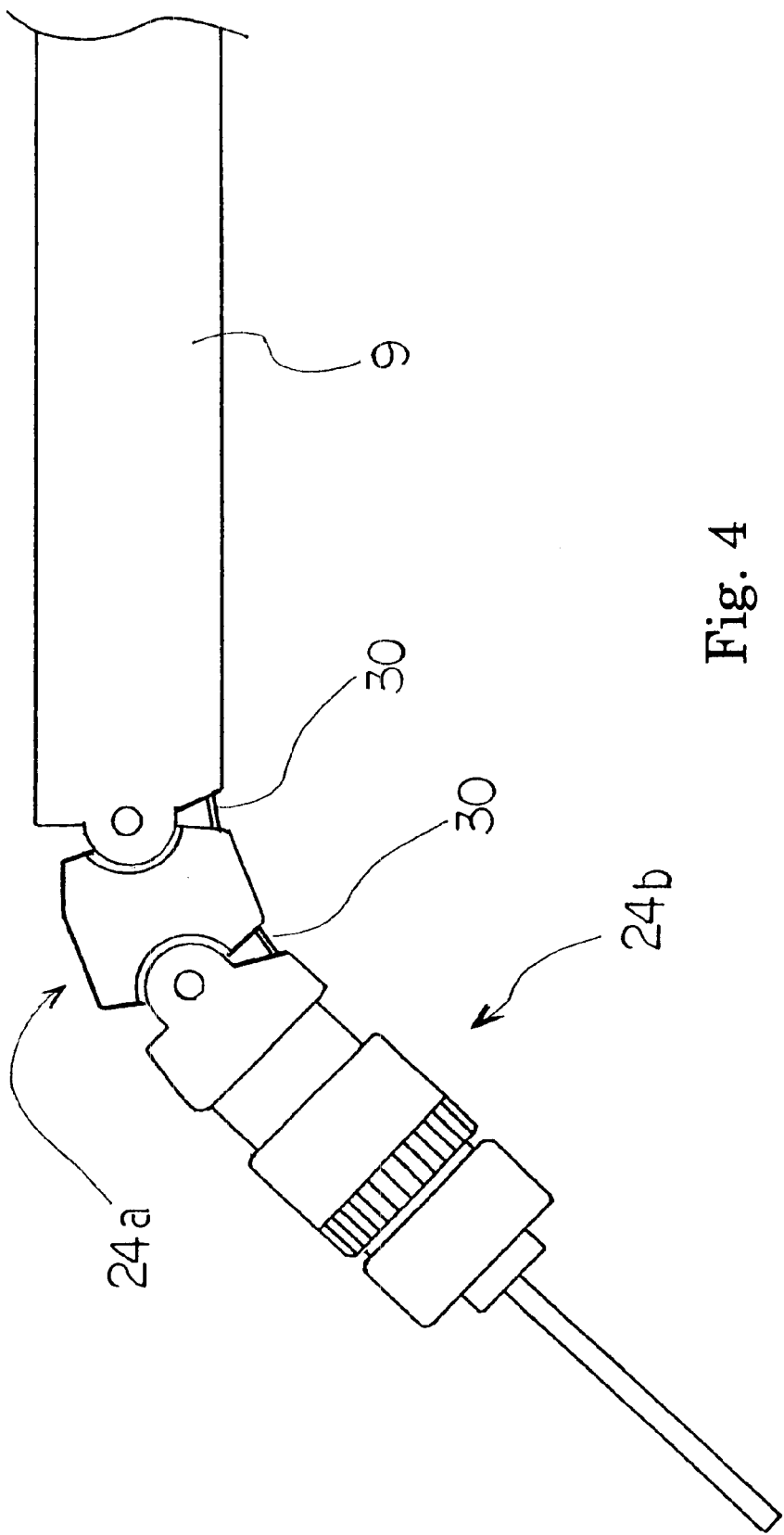
FIG. 4 illustrates an enlarged side view of and around the movable support in its curved position.

FIG. 4 is an enlarged side view of and around the movable support in a bent position resulted by a rightward pull of the spring member 30 relative to the support shaft 9. In the figure, the link 24b is angled at about 45° relative to the support shaft 9, whereas the angle of the link 24a is about a half of it. Thus, the overall curve of the movable support is substantially equally shared between the joints 22a and 22b. Therefore, the flexible coaxial cable extending therethrough is also evenly curved over these joints 22a and 22b, and acute concentration of curvature is thereby avoided at any one of the joints. This effect is also obtained where more joints are provided.

In the electrode device 1, which has two joints as illustrated in FIG. 1, the movable support 20 can be bent at any angle between 0° and 90°, at which the joints 22a and 22b substantially evenly share the angle of the curve, thus allowing a smooth curve of the flexible coaxial cable 10 contained therein. At any of its curved position, once the proximal end of the resilient member 30 is fixed at a corresponding location, the movable support 20 resists an external force tending to further bend or stretch itself, and its curved position is thereby kept stable. Thus it allows a reliable operation of inserting or pushing the central electrode 5 into or against the affected site at a desired angle, with the movable support 20 kept at a predetermined curved position. Thus, with the electrode device introduced into the abdominal cavity through a trocar inserted at a fixed site, coagulation of a given affected site can be performed from much less restricted angles than before, for one can securely apply the electrode to the affected site while freely controlling the curvature of the movable support.

When the spring member 30 is manipulated to return to its initial position, the force in the pressing back direction is transmitted through the spring member 30 and applied to the deflection side of the link 24b, thereby returning the movable support 20 to the stretched position shown in FIG. 3.

Figure 5:
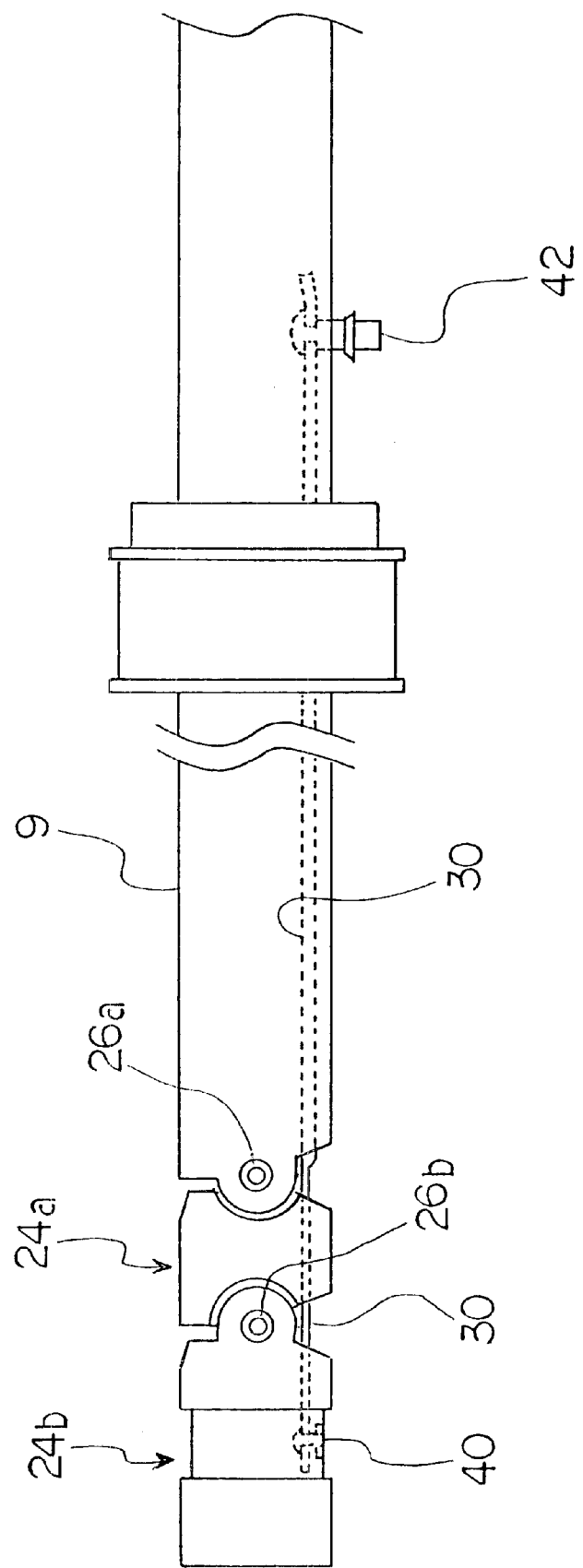
FIG. 5 illustrates an enlarged side view showing the mechanism for bending in further detail.
Figure 6:
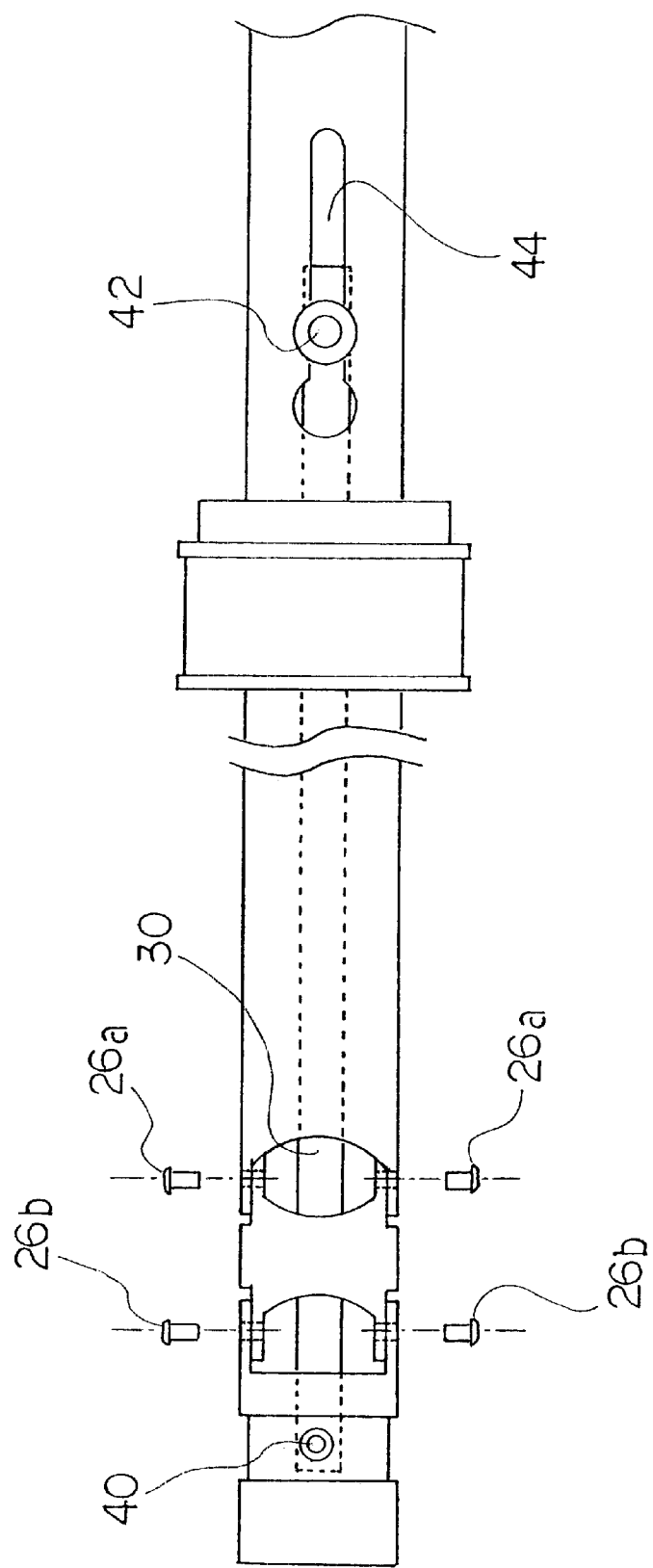
FIG. 6 illustrates an enlarged bottom view showing the mechanism for bending in further detail.

FIGS. 5 and 6 are enlarged side and bottom views, respectively, illustrating the mechanism for controlling the curve of the movable support 20 in greater detail, in which the flexible coaxial cable, the central electrode, the tubular ground electrode and the most part of the handpiece are not shown for convenience of explanation. In the figures, a pin 40 is inserted into the bores defined in the spring member 30 and the deflection side of link 24b and caulked to connect the spring member 30 to the deflection side of the link 24b. Each pair of pins 26a and 26b are also inserted into aligned bores defined in the support shaft and the link 24a or in the links 24a and 24b, respectively, and caulked to pivotally connect the links. The spring member 30 extends toward the handpiece 11 along the respective inner surfaces of the link 24a and the support shaft 9. Near the proximal end of the spring member 30 is fixedly provided a pin 42, one end of which protrudes out of a longitudinal slot 44 defined in the support shaft 9, which forms a tubular shaft portion of the handpiece 11.

Figure 7:
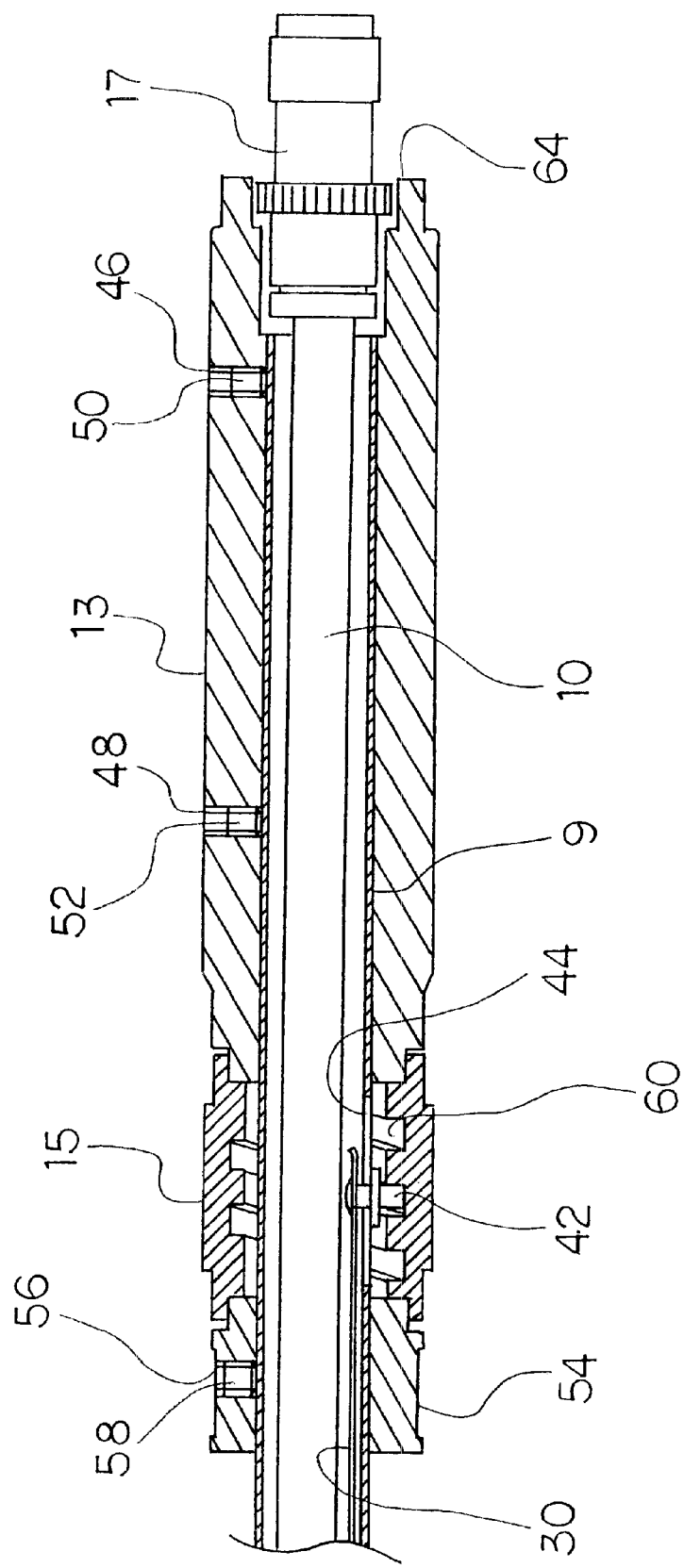
FIG. 7 illustrates a side cross-sectional view showing the structure of the handpiece.

FIG. 7 is a side sectional-view illustrating the structure of the handpiece 11. In the figure, the support shaft 9 extends nearly to the proximal end of the handpiece 11, thereby providing a tubular shaft section to the handpiece 11. The proximal end of the flexible coaxial cable 10 placed within the handpiece 11 is connected to a coaxial connector 17. A holding grip 13 which is a part of the handpiece 11 is secured onto the support shaft 9 by bolts 50 and 52 which are screwed into threaded bores 46 and 48 so as to exert pressure on the outer surface of the support shaft. An angle control ring 15, which serves as the control section, is placed between the holding grip 13 and a stopper ring 54, the latter of which is secured to the support shaft 9 by a bolt 58 screwed into a threaded bore 56. The angle control ring 15 can be rotated from outside, while it is blocked from shifting in the longitudinal direction by being sandwiched between the holding grip 13 and the stopper ring 54.

The angle control ring 15 is provided with an internal thread 60, with which engages the tip of the pin 42, which is secured to the spring member 30 and protrudes out of the slot 44 of the support shaft 9. By turning the angle control ring 15 from outside, the pin 42 engaging with the thread 60 is shifted in the longitudinal direction along the slot 44 relative to the support shaft 9, the spring member 30 is thereby pulled toward the proximal end or pushed back toward the distal end, and the movable support 20 connected to the distal end of the spring member 30 is then bent or stretched. Once the curve of the movable support 20 is adjusted to a desired angle, it is not necessary to continue to hold the angle control ring 15 with fingers, for even a force in the longitudinal direction applied to the spring member 30 could not rotate the angle control ring 15 because it would lock itself due to a superior frictional force generated between the thread 60 and the pin 42.

The coaxial connector 17 is partially inserted into the holding grip 13 in a longitudinally slidable manner. In the example of the electrode device 1 illustrated in FIG. 1, when the movable support 20 is bent, the distance from the handpiece to the distal end of the flexible coaxial cable 10 is shortened because the coaxial cable extending through the moving support 20 curves while shifting closer to the inner surface of the deflection side of the movable support 20. Therefore, if the coaxial connector 17 is fixed to the handpiece 11, a bending beyond a certain extent will cause the flexible coaxial cable 10 to be compressed in the longitudinal direction and a stress along the longitudinal axis is generated, which gives rise to a resistance against bending, thereby hindering a smooth manipulation. In this example of the present invention, instead, as the coaxial connector 17 can slide in the longitudinal direction to change its position and thereby no stress is generated in the direction of the longitudinal axis of the flexible coaxial cable, smooth bending is possible even at a large angle.

Figure 8:
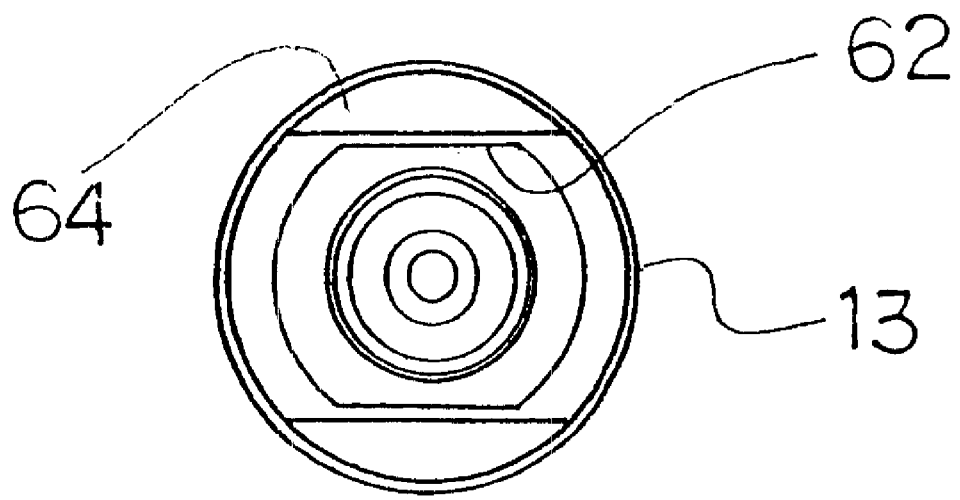
FIG. 8 illustrates an end view of the handpiece seen from its end where the coaxial connector attached.

FIG. 8 is an end view of the handpiece 11 seen from its end where the coaxial connector 17 is provided. In the figure, the coaxial connector 17 is provided with flat portions 62 in its periphery surrounding its outer surface, which flat portions 62 are so made that they, through engagement with guides 64 having flat surfaces defined in the holding grip 13, prevent rotation of the coaxial connector 17.

INDUSTRIAL APPLICABILITY

The present invention provides an electrode device for microwave coagulation therapy, which electrode allows the angle of its electrode tip to be freely controlled from a proximal region, thereby enabling to externally control the electrode inserted through a trocar into the abdominal cavity and applying it to the lesion from an optimal angle, thus enabling a smooth surgical operation and, by reducing restriction so far imposed according to the location of the lesion, widening the applicability of microwave coagulation therapy.

What is claimed is:

1. An electrode device for microwave surgery which allows control of the angle of the electrode thereof comprising:

a handpiece provided with a rigid hollow support shaft extending toward a distal end, a movable support provided at the distal end of said support shaft and carrying thereon an electrode for microwave surgery, a microwave coaxial cable which is connected at the proximal end thereof to a microwave coaxial connector and connected within said movable support to corresponding portions of the electrode for microwave surgery, said cable extending through said handpiece and said support shaft, wherein said movable support comprises one or more links surrounding said coaxial cable and longitudinally connected to the distal end of said support shaft, and said movable support can be bent and stretched, in a single plane, between the direction of the longitudinal axis of said support shaft and a direction deflected therefrom, wherein said electrode device further comprises a resilient stiff member fixed at one end thereof to the deflection side of said most distal one of the links composing the movable support and also connected to a control section of said handpiece movable from outside said handpiece, whereby said resilient stiff member can be pulled and pushed back at the proximal end of said handpiece, and said resilient stiff member extends through said support shaft, and wherein said coaxial connector is attached to said handpiece in a manner which allows said connector to shift in the longitudinal direction within a predetermined range so that said connector can follow a longitudinal shift of said coaxial cable resulting from a positional change of said movable support between bent and stretched positions.

2. An electrode device for microwave surgery according to claim 1, wherein said resilient stiff member comprises a metal belt or a metal wire.

3. An electrode device for microwave surgery according to claim 2, wherein said resilient stiff member is a metal member and the part of said metal member contained in the movable support is in the shape of a belt and the part contained in the support shaft is in the shape of a plate.

4. An electrode device for microwave surgery according to claim 2, wherein the resilient stiff member is a metal wire and is placed through a guide path provided along the inner surface of the support shaft.

5. An electrode device for microwave surgery of claim 1, wherein each of the links composing the movable support forms, with an adjacent link, a turning pair mutually pivotable around an axis perpendicular to the longitudinal axis of the support shaft.

6. An electrode device for microwave surgery of claim 1, wherein the control section comprises an internally threaded member which is fitted around a tubular shaft section of the hand-piece and prohibited from longitudinal shifting and which can be rotated from outside, wherein the thread of the internally threaded member associates with the proximal end of the resilient stiff member via a screw mechanism so that a rotation of the internally threaded member is converted to a longitudinal shift of the proximal end of the resilient stiff member.

7. An electrode device for microwave surgery of claim 6, wherein the proximal end of the resilient stiff member is fixedly provided with a projection directed radially outwardly, which protrudes out of a slot defined in the tubular shaft section of the handpiece and is slidable in the direction of the longitudinal axis and engages with the thread of the internally threaded member.

\* \* \* \* \*

UNITED STATES PATENT AND TRADEMARK OFFICE
CERTIFICATE OF CORRECTION

PATENT NO. : 6,451,014 B1
DATED : September 17, 2002
INVENTOR(S) : Wakikaido et al.

It is certified that error appears in the above-identified patent and that said Letters Patent is hereby corrected as shown below:

<u>Title page,</u>
Item [22], PCT Filed, delete "Jun. 5, 1999" and insert -- July 5, 1999 --.

Signed and Sealed this

Eighteenth Day of March, 2003

JAMES E. ROGAN
*Director of the United States Patent and Trademark Office*